United States Patent [19]
Hsu et al.

[11] Patent Number: 5,874,476
[45] Date of Patent: Feb. 23, 1999

[54] DIHALOFORMALDOXIME CARBAMATES AS ANTIMICROBIAL AGENTS

[75] Inventors: Adam Chi-Tung Hsu; Barry Clifford Lange, both of Landsdale; Jemin Charles Hsu, Fort Washington, all of Pa.

[73] Assignee: Rohm and Haas Company, Philadelphia, Pa.

[21] Appl. No.: 892,205

[22] Filed: Jul. 14, 1997

Related U.S. Application Data

[60] Provisional application No. 60/024,379 Aug. 14, 1996.
[51] Int. Cl.$^6$ ............... A61K 31/15; A61K 31/425; A01N 65/00
[52] U.S. Cl. ............... 514/640; 514/73; 514/372; 514/389; 514/557; 514/693; 514/694; 514/724
[58] Field of Search ............... 514/640, 372, 514/73, 589, 557, 724, 693, 694

[56] References Cited

U.S. PATENT DOCUMENTS

| | | | |
|---|---|---|---|
| 3,553,264 | 1/1971 | Addor | 552/204 |
| 3,742,036 | 6/1973 | Perronnet | 560/168 |
| 4,879,314 | 11/1989 | Hsu | 514/640 |
| 5,110,822 | 5/1992 | Sherba et al. | 514/372 |

FOREIGN PATENT DOCUMENTS

| | | |
|---|---|---|
| 1 535 082 | 10/1974 | France . |
| 556 138 | 11/1974 | Switzerland . |
| 958 631 | 5/1964 | United Kingdom . |
| 1 307 223 | 2/1973 | United Kingdom . |

OTHER PUBLICATIONS

Derwent Publications Ltd., London, GB, Section CH, Week 9410, Class C03, AN 94–077195, XP002047320 and JP 06 009 307 A (Junsei Kagaku KK), 18 Jan. 1994, abstract.

*Primary Examiner*—Kevin E. Weddington
*Attorney, Agent, or Firm*—Julie J. L. Cheng; S. Matthew Cairns

[57] ABSTRACT

Disclosed is a method of inhibiting the growth of microorganisms in, at, or on a locus subject to microbial attack, comprising introducing to said locus an antimicrobially effective amount of at least one dihaloformaldoxime carbamate.

10 Claims, No Drawings

DIHALOFORMALDOXIME CARBAMATES AS ANTIMICROBIAL AGENTS

BACKGROUND OF THE INVENTION

The present invention relates to a method for inhibiting the growth of microorganisms. In particular, the present invention relates to the use of certain dihaloformaldoxime carbamates as antimicrobial agents.

Antimicrobial agents are used commercially to prevent microbial growth in water cooling towers, metalworking fluid systems, paints, and other loci. Currently available antimicrobial agents include mixtures of 5-chloro-2-methyl-3-isothiazolone and 2-methyl-3-isothiazolones. While these isothiazolones are very effective in preventing microbial growth, they suffer from being slow killing and unstable under certain conditions. Nitrate salts are effective stabilizers for 3-isothiazolones, but the level of salt usually required can cause problems, such as coagulation of latices and salt build up in closed systems. There is therefore a continued need for antimicrobial agents which are stable, do not have a high salt content, have low use levels, provide quick speed of kill, degrade quickly upon use, and are safe to use in the environment.

U.S. Pat. No. 3,553,264 (Addor) discloses certain dihaloformaldoxime carbamates, methods for their preparation, and their use as postemergence herbicides. This patent also teaches the use of such dihaloformaldoxime carbamates as intermediates in the preparation of insecticides. This patent neither teaches nor suggests the use of such compounds as antimicrobial agents.

STATEMENT OF THE INVENTION

The present invention provides a method of inhibiting the growth of microorganisms in, at, or on a locus subject to microbial attack, comprising introducing to said locus an antimicrobially effective amount of at least one antimicrobial agent, wherein such antimicrobial agent is applied at low use levels, provides quick speed of kill, degrades quickly upon use, and is safe to use in the environment, such antimicrobial agent being of the formula:

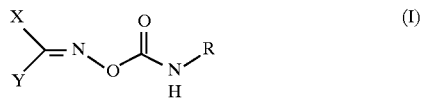
(I)

wherein: X, Y are independently selected from Br, Cl, or I; and R=($C_1$–$C_8$)alkyl, aryl, or substituted aryl.

DETAILED DESCRIPTION OF THE INVENTION

As used in this specification, the term "antimicrobial agent" refers both to a compound capable of inhibiting microbial growth (a preservative), and a compound capable of reducing microbial concentration (a disinfecting agent), within a given system. The term "antimicrobial activity" refers to the activity of the antimicrobial agents to eliminate, inhibit or prevent the growth of microorganisms. The terms "microbial organism," "microbe" and "microorganism" are used interchangeably and refer to microorganisms such as, but not limited to, fungi, bacteria, and algae. The following abbreviations are used throughout this specification: L=liter; mL=milliliter; g=grams; mol=moles; mmol=millimoles; wt %=percent by weight; mp=melting point. These antimicrobial agents are effective against microorganisms, including but not limited to: fungi, bacteria, and algae. Ranges specified are to be read as inclusive, unless specifically identified otherwise.

The compounds useful as antimicrobial agents in the present invention are those of formula (1), above. Preferred compounds of the present invention are those of formula (1) above, wherein X and Y are bromine. Especially preferred compounds of the present invention include the compounds listed in the following table.

| Cpd No. | Compound Name |
|---|---|
| 1 | N-methyl-dibromoformaldoxime carbamate |
| 2 | N-(2-chloroethyl)-dibromoformaldoxime carbamate |
| 3 | N-(4-chlorophenyl)-dibromoformaldoxime carbamate |
| 4 | N-(2,4-dichlorophenyl)-dibromoformaldoxime carbamate |
| 5 | N-ethyl-dibromoformaldoxime carbamate |
| 6 | N-(n-butyl)-dibromoformaldoxime carbamate |
| 7 | N-(n-octyl)-dibromoformaldoxime carbamate |
| 8 | N-(n-hexyl)-dibromoformaldoxime carbamate |
| 9 | N-(4-methylphenyl)-dibromoformaldoxime carbamate |

As used in this specification, "alkyl" means straight or branched chain ($C_1$–$C_{12}$)alkyl, and "substituted aryl" means an aryl group having one or more of its hydrogens replaced with another substituent group. Examples of suitable substituent groups include ($C_1$–$C_3$)alkyl, ($C_1$–$C_3$)alkoxy, hydroxy, nitro, halo, cyano, ($C_1$–$C_3$)alkylthio, and mercapto. Examples of substituted phenyl groups include 4-methylphenyl, 2-chlorophenyl, 3-chlorophenyl, 4-chlorophenyl, 2-methoxyphenyl, and 4-methoxyphenyl.

In the present invention, the carbamates of dibromoformaldoxime are generally synthesized by treating dibromoformaldoxime with alkyl or aryl isocyanates in methylene chloride in the presence of a catalyst, such as dibutyltin dilaurate, at a temperature between 0° and 25° C. The reaction time is between 2 and 48 hours, depending on the reactivity of the isocyanates. For example, the synthesis of N-butyl dibromoformaldoxime carbamate can be depicted by the following reaction scheme.

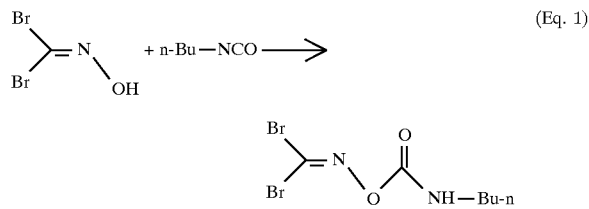
(Eq. 1)

The preparation of starting materials, dibromoformaldoxime and dichloroformaldoxime, are known in the literature. For example, the synthesis of dibromoformaldoxime can be found in *Tetrahedron Letters*, 25:487 (1984). This reference is hereby incorporated by reference to the extent it teaches preparation of dihaloformaldoximes.

The antimicrobial agents of the present invention can be used to inhibit the growth of microorganisms by introducing a microbicidally effective amount of one or more of said agents onto, into, or at a locus subject to microbial attack. Suitable loci include, but are not limited to: cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings, such as varnishes; construction products, such as mastics, caulks, and sealants; construction adhesives, such as ceramic adhesives, carpet backing adhesives, and laminating adhesives; industrial or consumer adhesives; photographic chemicals; printing fluids; household products, such as bathroom disinfectants or sanitizers; cosmetics and toiletries; shampoos; soaps; detergents; industrial disinfectants or sanitizers, such as cold sterilants, hard surface disinfectants; floor polishes; laundry rinse water; metalworking fluids; conveyor lubricants; hydraulic fluids; leather and leather products; textiles; textile products; wood and wood products, such as plywood, chipboard, flakeboard, laminated beams, oriented strandboard, hardboard, and particleboard; petroleum processing fluids; fuel; oilfield fluids, such as injection water, fracture fluids, and drilling muds; agriculture adjuvant preservation; surfactant preservation; medical devices; diagnostic reagent preservation; food preservation, such as plastic or paper food wrap; pools; and spas. Preferred loci are cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; and coatings.

The amount of antimicrobial agents of the present invention suitable to inhibit the growth of microorganisms depends upon the locus to be protected, but is generally between 0.05 and 10,000 ppm, based on the volume of said locus to be protected. It is preferred to use between 0.1 and 5000 ppm. For example, loci such as a cooling tower or pulp and paper processing fluids require 0.1 to 250 ppm of the compounds of the present invention to inhibit microorganism growth. In cooling towers or pulp and paper processing fluids, it is preferred to use between 0.1 and 50 ppm. Other loci, such as construction products, oilfield fluids or emulsions, require 0.5 to 5000 ppm of the compounds of the present invention to inhibit microorganism growth, while loci such as disinfectants or sanitizers may require up to 10,000 ppm.

It is known in the art that the performance of antimicrobial agents may be enhanced by combination with one or more other antimicrobial agents. Thus, other known antimicrobial agents may be combined advantageously with the antimicrobial agents of this invention. The compounds of the present invention may be combined with: methylenebis (thiocyanate); isothiazolones, such as 2-n-octyl-4-isothiazolin-3-one; 4,5-dichloro-2-n-octyl-4-isothiazolin-3-one; 5-chloro-2-methyl-4-isothiazolin-3-one; 2-methyl-4-isothiazolin-3-one; 1,2-benzisothiazolin-3-one; and 2-methyl-4,5-trimethylene-4-isothiazolin-3-one; carbamates, such as 3-iodopropargyl-N-butylcarbamate; methyl benzimidazol-2-ylcarbamate; imidazolidinyl urea; diazolidinyl urea; N'-[3,4-dichlorophenyl]-N,N-dimethylurea; 3,4,4'-trichlorocarbanilide; dimethyl dithiocarbamate; and disodium ethylene bisdithiocarbamate; heterocyclic compounds, such as zinc 2-pyridinethiol-1-oxide; sodium 2-pyridinethiol-1-oxide; 10,10'-oxybisphenoxyarsine; N-trichloromethylthiophthalimide; 5-oxo-3,4-dichloro-1,2-dithiol; 3-bromo-1-chloro-5,5-dimethylhydantoin; 4,4-dimethyl-1,3-dimethylolhydantoin; 2-(thiocyanomethylthio)benzothiazole; 2-methylthio-4-t-butylamino-6-cyclopropylamino-s-triazine; iodopolyvinylpyrrolidone; 3,5-dimethyl-1H-pyrazole-1-methanol; 1-(2-hydroxyethyl)-2-octadecylimidazoline; 4-(2-nitrobutyl)morpholine; triazine; N,N'-methylenebis(5-methyl-1,3-oxazolidine); 2,2'-oxybis(4,4,6-trimethyl-1,3,2-dioxaborinane); 2,2'-(1-methyltrimethylenedioxy) bis(4-ethyl-1,3,2-dioxaborinane); hexahydro-1,3,5-tris(2-hydroxyethyl)-s-triazine; 4,4-dimethyloxazolidine; 3,4,4-trimethyloxazolidine; 4,4'-(2-ethyl-nitrotrimethylene) dimorpholine; 2-methylthio-4-t-butylamino-6-cyclopropylamino-s-triazine; 2,3,5,6-tetrachloro-4-(methylsulfonyl)pyridine; alpha-[2-(4-chlorophenyl)ethyl]-alpha-(1,1-dimethylethyl)-1H-1,2,4-triazolyl-(1)-ethanol; 1-[(2-(2',4'-dichlorophenyl)-4-propyl-1,3-dioxolan-2-yl-methyl]-1H-1,2,4-triazole; didecyldimethylammonium chloride; copper-8-hydroxyquinoline; 1-[2-(2,4-dichlorophenyl)-1,3-dioxolan-2-yl-methyl]-1H-1,2,4-triazole; 2-(4-thiazolyl)-benzimidazole; 3,5-dimethyl-1,3,5-thiadiazine-2-thione; 2-chloro-4,6-bis(ethylamino)-1,3,5-triazine; 2-chloro-4-ethylamino-6-tert-butylamino-1,3,5-triazine; 1-(3-chloroallyl)-3,5,7-triaza-1-azoniaadamantane chloride; copper naphthenate; 5-hydroxymethoxymethyl-1-aza-3,7-dioxabicyclo[3.3.0]octane; 5-hydroxymethyl-1-aza-3,7-dioxabicyclo[3.3.0]octane; 7-ethyl-1,5-dioxa-3-azabicyclooctane; cetylpyridinium chloride; 3-bromo-1-chloro-5-dimethyl-5-ethylhydantoindodecyl-di(aminoethyl)-glycine; and 5-hydroxypoly-[methyleneoxyethyl]methyl-1-aza-3,7-dioxabicyclo[3.3.0]octane; oxidants, such as hydrogen peroxide; t-butyl hydrogen peroxide; cumene hydroperoxide; sodium or calcium hypochlorite; sodium or calcium hypobromite; dichloroisocyanuric acid; trichloroisocyanuric acid; peroxyacetic acid; ozone; chlorine; bromine; chlorine dioxide; potassium peroxymonosulfone; percarbonate; sodium perborate; bromamines; and bromine chloride; carboxylic acids and their derivatives, such as (E,E)-2,4-hexadienoic acid; benzoic acid; sodium or calcium propionate; ethylenediaminetetraacetic acid disodium salt; and sodium hydroxymethylglycinate; benzyl ester of 4-hydroxybenzoic acid; $(C_1–C_4)$alkyl esters of 4-hydroxybenzoic acid; $(C_1–C_4)$alkyl esters of 4-hydroxybenzoic acid sodium salts; dimethylamide of tall oil fatty acids; and 2,2-dibromo-3-nitrilopropionamide; alcohols and amines, such as 1-(alkylamino)-3-aminopropane; 2-bromo-2-nitro-1,3-propanediol; phenoxyethanol; benzyl alcohol; 2-hydroxymethylaminoethanol; n-2-hydroxypropylaminomethanol; 2-hydroxypropyl methanethiosulfonate; p-nitrophenol; and 4-chloro-3,5-dimethylphenol; ammonium and phosphonium salts, such as n-alkyl dimethyl benzylammonium chloride; cetyltrimethylammonium chloride; didecyldimethylammonium chloride; poly(hexamethylenebiguanide) hydrochloride; poly[oxyethylene(dimethyliminio) ethylene(dimethyliminio) ethylene dichloride]; alkyl dimethyl dichlorobenzylammonium chloride; dodecylguanidine hydrochloride; 2-(decylthio)ethaneamine hydrochloride; quaternary ammonium compounds; tetrakis(hydroxymethyl)phosphonium chloride; tetrakis(hydroxymethyl)phosphonium sulfate; aldehydes, ketones and formaldehyde releasers, such as pentane-1,5-dial; 1,2-benzenedicarboxaldehyde; formaldehyde; 2-bromo-4'-hydroxyacetophenone; tris(hydroxymethyl)nitromethane; and 5-bromo-5-nitro-1,3-dioxane; haolgenated aromatic compounds, such as 2,4,5,6-tetrachloroisophthalonitrile; 2,4,4'-trichloro-2'-hydroxydiphenyl ether; 2,2'-dihydroxy-5,5'-dichlorodiphenylmethane; and 1,6-di-(4'-chlorophenyldiguanide)-hexane; halogenated aliphatic compounds, such as 1,2-dibromo-2,4-dicyanobutane; diiodomethyl-p-tolysulfone; dibromonitroethane; hexachlorodimethylsulfone; alkenes, such as β-bromo-β-nitrostyrene; 1,4-bis(bromoacetoxy)-2-butene; terpene; and limonene; inorganic compounds, such as bismuth; copper; silver; copper amine complexes; mono copper nitrate; borate salts; zinc oxide; sodium bromide; ammonium bromide; disodium octaborate tetrahydrate; tributyltin oxide; and chromated copper arsenate; enzymes, such as cellulase; alpha-amylase; protease; polysaccharidase; levan hydrolase; and surfactants, such as alkyl aryl esters, polyethoxylated alcohols, polyoxyethylated ethers, phosphate esters, sulfonates, sulfonated fatty materials, sulfosuccinates, and dodecylbenzene sulfonic acids.

Preferred known antimicrobial agents to be combined with the antimicrobial agents of the present invention are methylenebis(thiocyanate); 5-chloro-2-methyl-4-isothiazolin-3-one; 2-methyl-4-isothiazolin-3-one; as 2-n-octyl-4-isothiazolin-3-one; 4,5-dichloro-2-n-octyl-4-isothiazolin-3-one; 1,2-benzisothiazolin-3-one; zinc 2-pyridinethiol-1-oxide; sodium 2-pyridinethiol-1-oxide; N'-[3,4-dichlorophenyl]-N,N-dimethylurea; 3-iodopropargyl-N-butylcarbamate; 10,10'-oxybisphenoxyarsine; 2-(thiocyanomethylthio) benzothiazole; 3-bromo-1-chloro-5,5-dimethylhydantoin; 2,2-dibromo-3-nitrilopropionamide; pentane-1,5-dial; and 2-bromo-2-nitro-1,3-propanediol.

The compounds of the present invention may also be used in conjuction with non-chemical methods of microbial control, such as ultraviolet light; ionizing radiation; copper electrodes; silver electrodes; and enzymes, such as cellulase, alpha-amylase, protease, polysaccharidase, and levan hydrolase.

If one of the antimicrobial agents of the invention is to be combined with a second antimicrobial agent, the weight ratio of the first antimicrobial agent to the second antimicrobial agent is 99:1 to 1:99; preferably, 75:25 to 25:75. The total of the combined antimicrobial agents necessary to inhibit or prevent the growth of microbes is generally 0.05 to 10,000 ppm, based on the volume of said locus to be protected.

The antimicrobial agents of the present invention may be added directly to a locus to be protected or may be added as a formulation. The antimicrobial agents of the present invention may be formulated in a variety of liquid or solid formulations. The particular type (that is, solid or liquid) and composition of the formulation used will depend on the locus to be protected and the characteristics of the formulation sought. For example, where splash hazards are a concern or where controlled release is desired, solid formulations may be preferred. Liquid formulations may be preferred where the formulation is metered into a locus over a period of time. Solid formulations are particularly useful in loci such as cooling towers, latexes, and plastics. Liquid formulations are particularly useful in loci such as paints, cosmetics; household cleaners; and water treatment applications.

In general, the antimicrobial agents of the present invention may be formulated in liquid form by dissolving the antimicrobial agent in a carrier. Suitable carriers include water, organic solvent, or mixtures thereof. Any organic solvent is suitable as long as it is compatible with the end use and does not destabilize the antimicrobial agent. Suitable organic solvents include, but are not limited to: aliphatic and aromatic hydrocarbons, such as xylene and mixtures of alkylbenzenes; halogenated aliphatic and aromatic hydrocarbons, such as ethylene dichloride and monochlorobenzene; alcohols, such as monohydric, dihydric, and polyhydric alcohols; aldehydes; ketones, such as acetone, methyl ethyl ketone, and methyl iso-butyl ketone; ethers; glycol ethers; glycol ether acetates; saturated and unsaturated fatty acids having at least four carbon atoms; esters, such as ethyl acetate, butyl acetate, glycol esters, and phthalate esters; and phenols. Preferred organic solvents are glycol ethers; glycol ether acetates; aliphatic and aromatic hydrocarbons; and alcohols.

Aqueous formulations of the antimicrobial agents of the present invention may be prepared as dispersions, such as polymeric dispersions; emulsions; emulsive concentrates; microemulsions; and microemulsive concentrates. The dispersions, emulsions, and microemulsions can have either oil continuous or water continuous phases. Aqueous formulations typically contain 0.001 to 50 wt % of the antimicrobial agent of the present invention, up to 99 wt % organic solvent, 0.5 to 55 wt % surfactant, up to 15 wt % adjuvants, and up to 95 wt % water. Suitable surfactants are anionic, such as alkyllauryl sulfonate salts and fatty alcohol ethoxylate sulfates; cationic; nonionic, such as ethylene oxide-propylene oxide copolymers; and amphoteric. Typical adjuvants suitable for use in aqueous formulations include, but are not limited to: thickeners, anti-freeze agents, and defoamers.

Suitable solid formulations of the antimicrobial agents of the present invention include, but are not limited to: polymeric encapsulants, such as those prepared by interfacial condensation, coacervation, in-situ polymerization, and physical methods; inclusion complexes, such as clathrates; liposomes; matrix blends, such as granulars, dispersible granulars, and wettable powders; and ion exchange resins. Polymeric encapsulants can be prepared having either a core shell or monolithic structure. Suitable polymeric encapsulants include, but are not limited to: polyureas, polyamides, polyesters, urea-formaldehydes, melamine-formaldehydes, polyacrylic acid and its esters, phenol-formaldehydes, and acetoacetates.

Inclusion complexes may be prepared by incorporating the antimicrobial agent of the present invention in a host molecule. Suitable host molecules include, but are not limited to: α-cyclodextrin; β-cyclodextrin; γ-cyclodextrin; cyclodextrin derivatives, such as methyl-β-cyclodextrin; crown ethers; ureas; hydroquinones; dichlorophene; hydroxybenzophenone; and 1,1,2,2-tetrakis(4-hydroxyphenyl)ethane. The inclusion complex can be used as a solid composition, adsorbed onto a solid carrier, or dispersed in a non-reactive solvent. Inclusion complexes are useful in water treatment, metalworking fluid, and paint applications.

Liposomes can be prepared by dissolving the antimicrobial agents of the present invention and a lipid, such as a phospholipid, in a suitable solvent, such as chloroform. The solvent is removed, a buffer added, and the composition is agitated to produce the desired particle size. The liposomes may be multilamellar, unilamellar, or have large or small particle size. Liposomes are useful in solvent based paint and cosmetics applications.

Matrix blends can be prepared by adsorbing the antimicrobial agents of the present invention onto a solid carrier with the addition of appropriate additives in order to make granulars, wettable powders, and dispersible granulars. These matrix blends may be used as is or may be further be processed into pellets, tablets, or briquettes by any conventional means. Granulars typically comprise 1 to 60 wt % antimicrobial agent of the present invention; 30 to 98 wt % of an absorbent carrier, such as diatomaceous earth, water soluble solids, magnetic particles, or fumed inorganics, such as silica, titania, and zinc oxide; and 1 to 10 wt % adjuvants. Wettable powders typically comprise 1 to 60 wt % antimicrobial agent of the present invention; 1 to 5 wt % wetting agent; 1 to 20 wt % dispersant; 10 to 95 wt % adsoptive carrier, such as fumed inorganics or clay; and up to 10 wt % adjuvants. Dispersible granulars typically comprise 1 to 60 wt % antimicrobial agent of the present invention; 30 to 95 wt % adsoptive carrier, such as fumed inorganics or clay; 5 to 40 wt % dispersant; up to 10 wt % surfactant; and up to 15 wt % adjuvant. Dispersible granulars may be further extruded, dried and processed into granulars.

The following examples are presented to illustrate further various aspects of the present invention, but are not intended to limit the scope of the invention in any respect.

EXAMPLE 1

Preparation of N-(n-butyl)-dibromoformaldoxime carbamate

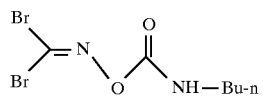

To a solution of dibromoformaldoxime (11.8 g, 0.058 mol) in methylene chloride (20 mL) in an ice bath under nitrogen with magnetic stirring was added 6.9 g of n-butyl isocyanate (0.058 mol) followed by a catalytic amount (8 drops) of dibutyltin dilaurate. The reaction mixture was further stirred at room temperature for 16 hours. The mixture was then washed with diluted sodium bicarbonate solution (2×50 mL), water (5×25 mL) and brine (50 mL). The organic layer was dried over $MgSO_4$ and filtered. The filtrate was concentrated in vacuum to give 4.9 g of a yellow oil. A purer yellow oil, 12.1 g (yield 69%), was obtained by column chromatography using silica gel and eluting with hexane-:ethyl acetate (9:1).

Elemental analysis for $C_6H_{10}Br_2N_2O_2$ indicated the following. Calculated: C=23.86%; H=3.34%; N=9.28%; Br=52.92%. Found: C=24.07%; H=3.47%; N=9.31%; Br=52.85%.

EXAMPLE 2

Preparation of N-(4-methylphenyl)-dibromoformaldoxime carbamate

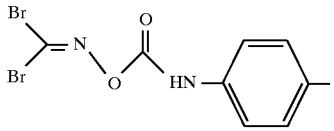

To a solution of dibromoformaldoxime (2 g, 9.86 mmol) in methylene chloride (20 mL) in an ice bath under nitrogen with magnetic stirring was added 4-methylphenyl isocyanate (1.6 g, 12 mmol) and a catalytic amount of dibutyltin dilaurate (5 drops). The reaction mixture was stirred at room temperature for 16 hours. The reaction mixture was washed with water (3×50 mL) and brine. The organic layer was dried over $MgSO_4$ and filtered. The filtrate was concentrated in vacuum to give a crude product which was purified by a column silica gel eluting with hexane:ethyl acetate (8:1) yielding an off white solid, 1.7 g (yield: 51%). mp=120°–124° C.

Elemental analysis for $C_9H_8Br_2N_2O_2$ indicated the following. Calculated: C=32.10%; H=2.40%; N=8.34%; Br=47.57%. Found: C=33.76%; H=2.35%; N=8.55%; Br=50.12%.

EXAMPLE 3

Efficacy

The spectrum of antimicrobial activity and the effect of anionic surfactant on the antimicrobial activity of the antimicrobial agents useful in the present invention were determined in Minimum Inhibitory Concentration (MIC) tests. MICs were determined by two fold serial dilutions of a compound in Minimal Salts Media (M9G), Trypticase Soy Broth (TSB) or Tryticase Soy Broth and anionic surfactant (TSBA). The compounds were tested against *Aspergillus niger*, *Rhodotorula rubra*, *Escherichia coli* and *Pseudomonas aeruginosa*. Results of the MIC tests are shown below.

TABLE 1

| Compound | E. Coli M9G | E. Coli TSB | P. aeruginosa TSB | A. niger TSB | R. Rubra TSB | E. coli TSBA |
|---|---|---|---|---|---|---|
| 3 | <4 | 63 | 63 | >50 | >50 | 63 |
| 6 | <4 | 250 | 63 | >50 | >50 | 63 |
| 7 | <4 | 63 | >500 | 50 | 12.5 | 125 |
| 8 | <4 | 63 | 125 | >50 | 25 | 32 |
| 9 | <4 | 32 | 16 | <0.8 | 3.2 | 32 |

The above results show that Compounds 3, 6, 7, 8, and 9 are surprisingly effective at controlling microorganisms in, at, or on a locus.

EXAMPLE 4

Speed of Kill

The speed of kill for various compounds of the present invention were determined according to the following procedure.

A solution of 5% alpha olefin sulfonate (AOS) was prepared by weighing 5 g of 40% AOS into a 100 mL flask, adding 35 mL of deionized water, and swirling the solution. The solution was then filter sterilized.

Trypticase soy broth (TSB) medium was prepared by weighing 30 g TSB into a 2 L flask, adding 1 L of deionized water, and swirling the flask until the TSB was completely dissolved. The medium was then autoclaved at 121° C. for 20 minutes.

A solution of TSB+0.05% AOS was prepared by adding 1 mL of sterile 5% AOS to 100 mL of sterile TSB in a 250 mL flask, followed by swirling of the solution.

A nutrient stock solution was prepared by weighing the following into a 2 L flask: 5.28 g of ammonium nitrate, 2.08 g of anhydrous potassium phosphate, 4.62 g of dextrose, 21.50 g of sodium carbonate, and 40.20 g of potassium sulfate. The total volume was adjusted up to 1 L with water, and the flask was swirled until all solids were dissolved. The solution was then filter sterilized and stored at room temperature.

A hardness stock was prepared by weighing the following into a 2 L flask: 59.36 g of calcium chloride (dihydrate), 45.02 g of magnesium chloride (hexahydrate), 0.18 g of ferric chloride (hexahydrate), 0.06 g of cupric chloride (dihydrate), and 0.24 g of sodium ethylenediaminetetraacetic acid. The total volume was adjusted up to 1 L with water. The solution was filter sterilized and stored at room temperature.

A concentrated corrosion/scale inhibitor stock was prepared by weighing into a 2 L flask: 238.5 g of deionized water, 125.0 g of a 45% wt aqueous solution of potassium hydroxide, 23.0 g of a 50% wt aqueous solution of sodium tolyltriazole, 63.5 g of a 42–44% wt aqueous acrylic polymer, and 50.0 g of an approximately 50% wt aqueous solution of 2-phosphono-1,2,4-butanetricarboxylic acid. The flask was swirled until all solids were dissolved, and then the solution was filter sterilized and stored at room temperature.

This concentrated corrosion/scale inhibitor stock solution was used to prepare a corrosion/scale inhibitor stock solution by adding 9.20 mL of the concentrated corrosion/scale inhibitor stock solution to a 2 L flask, and adjusting the volume up to 1 L with water, with swirling. The resultant corrosion/scale inhibitor stock solution was filter sterilized and stored at room temperature.

A synthetic cooling water ("SCW") was prepared by adding 900 mL of deionized water and 10.88 mL of the nutrient stock (pH 10–13) into a 2 L flask. The pH was adjusted down to pH 6, then 10.88 mL of the hardness stock was added. This was followed by addition of 10.88 mL of the corrosion/scale inhibitor stock. The pH was then adjusted to 8, and the final volume adjusted to 1 L with deionized water. This final solution was filter sterilized and stored at room temperature.

The inocula were prepared by inoculating 2 TSB agar slants with a loopful of culture from freezer stock cultures. The slants were then incubated at 30° C. for 2 days. The cells were washed off each slant with 15 mL of sterile phosphate buffer (pH 7.2). The cell concentrations were adjusted to 0.2 OD at 600 nm (corresponding to about $1-2\times10^8$ bacteria/mL). The working stocks were stored at 4° C. for no more than 4–6 weeks. If additional working stocks were required after 6 weeks, fresh stocks were prepared. The following organisms were used to create the stock culture:

|  | ATCC |
| --- | --- |
| Pseudomonas aeruginosa | 15442 |
| Klebsiella pneumonia | 13883 |
| Enterobacter aerogenes | 13048 |

The speed of kill test was performed as follows: 150 μL sterile SCW was dispensed into 96 well microtiter plates and an extra 150 μL was added to the top row of wells. Test compounds were added from 1% or lower stocks to give desired starting concentrations of 250 ppm or 150 ppm. Two-fold serial dilutions were done using a 12-channel pipetor. All wells were inoculated simultaneously with 1.5 μL of a mixture of working stock cultures at 1:1:1 ratio using the 96 pin Dynatech® MIC 2000 inoculator. This gave a final concentration of $10^6$ cells per mL. Inoculated plates were stored at ambient temperature. At 4 and 24 hours, viable cells in each well were recovered by transferring 1.5 μL into 150 μL TSB+0.05% AOS using the 96 pin inoculator. The recovery plates were incubated for 48 hours at 30° C. Growth (+) or no growth (−) in the recovery plates was recorded, indicating the concentration and time to achieve at least a two log reduction of the inoculated cells. Results are shown below.

TABLE 2

| Compound | Effective Concentration (ppm) | |
| --- | --- | --- |
|  | 4 Hours | 24 Hours |
| 3 | 8 | <4 |
| 6 | 16 | 16 |
| 8 | <4 | <4 |
| 9 | 125 | 8 |

The above results show that Compounds 3, 6, 8, and 9 have a quick speed of kill in synthetic cooling water, and that the compounds are effective at low use levels.

What is claimed is:

1. A method of inhibiting the growth of microorganisms in, at, or on a locus subject to microbial attack, comprising introducing to said locus an antimicrobially effective amount of at least one antimicrobial agent, wherein such antimicrobial agent is applied at low use levels, provides quick speed of kill, degrades quickly upon use, and is safe to use in the environment, such antimicrobial agent being of the formula:

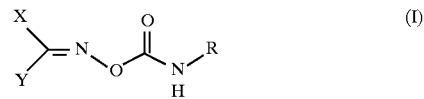

wherein: X, Y are independently selected from Br, Cl, or I; and R=($C_1$–$C_8$)alkyl, aryl, or substituted aryl.

2. The method of claim 1 wherein X=Y=Br.

3. The method of claim 2 wherein said antimicrobial agent is selected from the group consisting of N-methyl-dibromoformaldoxime carbamate; N-(2-chloroethyl)-dibromoformaldoxime carbamate; N-(4-chlorophenyl)-dibromoformaldoxime carbamate; N-(2,4-dichlorophenyl)-dibromoformaldoxime carbamate; N-ethyl-dibromoformaldoxime carbamate; N-(n-butyl)-dibromoformaldoxime carbamate; N-(n-octyl)-dibromoformaldoxime carbamate; N-(n-hexyl)-dibromoformaldoxime carbamate; and N-(4-methylphenyl)-dibromoformaldoxime carbamate.

4. The method of claim 1 wherein said locus is selected from the group consisting of cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; coatings; lazures; construction products; construction adhesives; industrial or consumer adhesives; photographic chemicals; printing fluids; household products; cosmetics and toiletries; shampoos; soaps; detergents; industrial disinfectants or sanitizers; floor polishes; laundry rinse water; metalworking fluids; conveyor lubricants; hydraulic fluids; leather and leather products; textiles; textile products; wood and wood products; petroleum processing fluids; fuel; oilfield fluids; surfactant preservation; medical devices; diagnostic reagent preservation; food preservation; pools; and spas.

5. The method of claim 1 wherein said antimicrobially effective amount is from 0.05 to 10,000 ppm based on the weight of said locus.

6. The method of claim 5 wherein said antimicrobially effective amount is from 0.1 to 5000 ppm based on the weight of the locus.

7. The method of claim 1 wherein:
(a) said locus is selected from the group consisting of cooling towers; air washers; boilers; mineral slurries; wastewater treatment; ornamental fountains; reverse osmosis filtration; ultrafiltration; ballast water; evaporative condensers; heat exchangers; pulp and paper processing fluids; plastics; emulsions and dispersions; paints; latexes; and coatings;
(b) said antimicrobially effective amount is from 0.1 to 5000 ppm; and
(c) said antimicrobial agent is selected from the group consisting of N-methyl-dibromoformaldoxime carbamate; N-(2-chloroethyl)-dibromoformaldoxime carbamate; N-(4-chlorophenyl)-dibromoformaldoxime carbamate; N-(2,4-dichlorophenyl)-dibromoformaldoxime carbamate; N-ethyl-dibromoformaldoxime carbamate; N-(n-butyl)-dibromoformaldoxime carbamate; N-(n-octyl)-dibromoformaldoxime carbamate; N-(n-hexyl)- dibromoformaldoxime carbamate; and N-(4-methylphenyl)-dibromoformaldoxime carbamate.

8. The method of claim 1 further comprising a second antimicrobial agent selected from the group consisting of: methylenebis(thiocyanate); isothiazolones; carbamates; heterocyclic compounds; oxidants; carboxylic acids and their derivatives; alcohols and amines; ammonium and phosphonium salts; aldehydes, ketones and formaldehyde releasers; haolgenated aromatic compounds; halogenated aliphatic compounds; alkenes; inorganic compounds; enzymes; and surfactants.

9. The method of claim 8 wherein said second antimicrobial agent is selected from the group consisting of 5-chloro-2-methyl-4-isothiazolin-3-one; 2-methyl-4-isothiazolin-3-one; as 2-n-octyl-4-isothiazolin-3-one; 4,5-dichloro-2-n-octyl-4-isothiazolin-3-one; 1,2-benzisothiazolin-3-one; zinc 2-pyridinethiol-1-oxide; sodium 2-pyridinethiol-1-oxide; N'-[3,4-dichlorophenyl]-N,N-dimethylurea; 3-iodopropargyl-N-butylcarbamate; 10,10'-oxybisphenoxyarsine; 2-(thiocyanomethylthio) benzothiazole; 3-bromo-1-chloro-5,5-dimethylhydantoin; 2,2-dibromo-3-nitrilopropionamide; pentane-1,5-dial; and 2-bromo-2-nitro-1,3-propanediol.

10. An antimicrobial composition comprising:

(a) an antimicrobial agent of the formula:

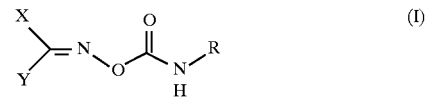

(I)

wherein: X, Y are independently selected from bromo, chloro, or iodo; and R=$(C_1–C_8)$alkyl, aryl, or substituted aryl; and (b) a second antimicrobial agent selected from the group consisting of: methylenebis(thiocyanate); isothiazolones; carbamates; heterocyclic compounds; oxidants; carboxylic acids and their derivatives; alcohols and amines; ammonium and phosphonium salts; aldehydes, ketones and formaldehyde releasers; halogenated aromatic compounds; halogenated aliphatic compounds; alkenes; inorganic compounds; enzymes; and surfactants.

* * * * *